United States Patent
De Leval

(10) Patent No.: US 7,611,454 B2
(45) Date of Patent: Nov. 3, 2009

(54) SURGICAL PROCEDURE FOR THE TREATMENT OF FEMALE URINARY INCONTINENCE: TENSION-FREE INSIDE-OUT TRANSOBTURATOR URETHRAL SUSPENSION

(75) Inventor: Jean De Leval, Louveigne (BE)

(73) Assignees: Universite De Liege, Liege (BE); Centre Hospitalier Universitaire De Liege, Liege (BE)

( * ) Notice: Subject to any disclaimer, the term of this patent is extended or adjusted under 35 U.S.C. 154(b) by 786 days.

(21) Appl. No.: 10/854,140

(22) Filed: May 27, 2004

(65) Prior Publication Data

US 2005/0021086 A1  Jan. 27, 2005

Related U.S. Application Data

(63) Continuation-in-part of application No. 10/628,251, filed on Jul. 29, 2003, now Pat. No. 7,204,802.

(60) Provisional application No. 60/406,674, filed on Aug. 29, 2002, provisional application No. 60/419,967, filed on Oct. 22, 2002, provisional application No. 60/427,213, filed on Nov. 19, 2002, provisional application No. 60/445,817, filed on Feb. 10, 2003.

(51) Int. Cl.
 *A61F 2/02* (2006.01)
(52) U.S. Cl. .................................................. 600/30
(58) Field of Classification Search .............. 606/222, 606/227, 139, 141, 144, 223–226, 184, 185, 606/148; 600/29, 30, 31, 37; 128/898, DIG. 25
See application file for complete search history.

(56) References Cited

U.S. PATENT DOCUMENTS

| | | | |
|---|---|---|---|
| 5,112,344 A | 5/1992 | Petros | 606/148 |
| 5,899,909 A | 5/1999 | Claren et al. | 606/119 |
| 6,273,852 B1 | 8/2001 | Lehe et al. | 600/30 |
| 6,475,139 B1 | 11/2002 | Miller | 600/135 |
| 6,494,887 B1 | 12/2002 | Kaladelfos | 606/148 |
| 6,605,097 B1 | 8/2003 | Lehe et al. | 606/148 |
| 6,612,977 B2 | 9/2003 | Staskin et al. | 600/30 |
| 6,641,525 B2 | 11/2003 | Rocheleau et al. | 600/30 |
| 6,652,450 B2 | 11/2003 | Neisz et al. | 600/30 |
| 6,911,003 B2* | 6/2005 | Anderson et al. | 600/30 |
| 7,244,259 B2* | 7/2007 | Smith et al. | 600/29 |
| 7,371,245 B2 | 5/2008 | Evans et al. | 606/151 |

(Continued)

FOREIGN PATENT DOCUMENTS

EP  1159921 A2  12/2001

(Continued)

OTHER PUBLICATIONS

Delorme, Prog Urol. Feb. 2003, 13(1), p. 117, Bladder injury after TVT transobturator.

(Continued)

*Primary Examiner*—Kevin T Truong
(74) *Attorney, Agent, or Firm*—Jacobson Holman PLLC

(57) ABSTRACT

A new, quick, simple, efficient, safe, and reproducible surgical technique for the treatment of female urinary incontinence, in which the posterior urethra is suspended using a tape passed through the obturator orifices from inside (underneath the urethra) to outside (thigh folds). A variety of specifically designed surgical instruments are utilized to perform this operative procedure.

2 Claims, 14 Drawing Sheets

U.S. PATENT DOCUMENTS

| | | | |
|---|---|---|---|
| 2002/0050277 A1 | 5/2002 | Beyar | 128/898 |
| 2002/0099258 A1 | 7/2002 | Staskin et al. | 600/29 |
| 2002/0099259 A1 | 7/2002 | Anderson et al. | 600/29 |
| 2002/0099260 A1 | 7/2002 | Suslian et al. | 600/30 |
| 2002/0107430 A1 | 8/2002 | Neisz et al. | 600/37 |
| 2002/0147382 A1 | 10/2002 | Neisz et al. | 600/29 |
| 2002/0151762 A1 | 10/2002 | Rocheleau et al. | 600/30 |
| 2002/0161382 A1 | 10/2002 | Neisz et al. | 600/151 |
| 2003/0045774 A1 | 3/2003 | Staskin et al. | 600/29 |
| 2003/0050530 A1 | 3/2003 | Neisz et al. | 600/29 |
| 2003/0065246 A1 | 4/2003 | Inman et al. | 600/29 |
| 2003/0130670 A1 | 7/2003 | Anderson et al. | 606/151 |
| 2003/0171644 A1 | 9/2003 | Anderson et al. | 600/29 |
| 2003/0176875 A1 | 9/2003 | Anderson et al. | 606/151 |
| 2003/0212305 A1 | 11/2003 | Anderson et al. | 600/29 |
| 2004/0015048 A1 | 1/2004 | Neisz et al. | 600/37 |
| 2004/0015057 A1 | 1/2004 | Rocheleau et al. | 600/300 |
| 2004/0039453 A1 | 2/2004 | Anderson et al. | 623/23 |
| 2004/0068159 A1 | 4/2004 | Neisz et al. | 600/29 |
| 2004/0106845 A1 | 6/2004 | Anderson et al. | 600/30 |

FOREIGN PATENT DOCUMENTS

| | | |
|---|---|---|
| WO | WO00/74594 | 12/2000 |
| WO | WO02/26108 | 4/2002 |
| WO | WO02/32284 | 4/2002 |
| WO | WO02/39890 | 5/2002 |
| WO | WO02/45774 | 6/2002 |
| WO | WO02/058562 | 8/2002 |
| WO | WO02/058563 | 8/2002 |
| WO | WO02/058564 | 8/2002 |
| WO | WO02/058565 | 8/2002 |
| WO | WO02/062237 | 8/2002 |
| WO | WO02/078571 | 10/2002 |
| WO | WO03/069781 | 8/2003 |
| WO | WO03/075792 | 9/2003 |
| WO | WO2004/034912 | 4/2004 |

OTHER PUBLICATIONS

Costa et al, European Urology 46, 2004, pp. 102-107, Surgical Treatment of Female Stress Urinary Incontinence with a . . . .

Delorme et al, European Urology, 45, 2004, pp. 203-207, Trans-obturator Tape (Uratape®) : A New Minimally-Invasive Procedure . . . .

de Leval, European Urology 44, 2003, pp. 724-730, Novel Surgical Technique for the Treatment of Female Stress Urinary . . . .

de Leval, Ltrs to the Editor/European Urology 46, 2004, pp. 134-137, Reply to V. Delmas.

Ulmsten et al, Int Urogynecol J 7, 1996, pp. 81-86, An Ambulatory Surgical Procedure Under Local Anesthesia for Treatment . . . .

Haab et al, Urology 11, 2001, pp. 293-297, Tension-free vaginal tape: why an unusual concept is so successful.

Nilsson et al, Int Urogynecol J, Supply 2, 2001, pp. S5-S8, Long-term Results of the Tension-Free Vaginal Tape (TVT) . . . .

Neuman, Jour of Urology, vol. 168, Dec. 2002, p. 2549, Infected Hematoma Following Tension-Free Vaginal Tape Implantation.

Shobeiri et al, Int Urogynecol J 14, 2003, pp. 185-190, The anatomy of midurethral slings and dynamics of neurovascular . . . .

Meschia et al, Int Urogynecol J, Supp 2, 2001, pp. S24-S27, Tension-Free Vaginal Tape: Analysis of Outcomes and . . . .

Fourie et al, Int Urogynecol J 14, 2003, pp. 362-364, Delayed bowel erosion by tension-free vaginal tape (TVT).

Meschia et al, Int Urogynecol J 13, 2002, pp. 263-265, Bowel Perforation During Insertion of Tension-free Vaginal Tape (TVT).

Sergent et al, Proges En Urologie 13, 2003, pp. 648-655, Complications per et post-operatoires du TVT (Tension-free . . . .

Kuuva et al, Acta Obstet Gynecol Scand 81, 2002, pp. 72-77, A nationwide analysis of complications associated with the . . . .

Delorme et al, Progres En Urologie 13, 2003, pp. 656-659, Transobturator tape (Uratape®), a new minimally (see Summary).

deTayrac et al, Amer Jour of Obstet & Gyncol 190, 2004, pp. 602-608, A prospective randomized trial comparing tension-free . . . .

Whiteside et al, Int Urogynecol J 15, 2004, pp. 223-226, Anatomy of the obturator region: relations to a trans- . . . .

Game et al, Jour of Urology, vol. 171, Apr. 2004, p. 1629, Obturator Infected Hematoma and Urethral Erosion Following . . . .

Sanjurjo et al, Rev Med Liege 57:12, 202, pp. 765-770, TVT: Revolutionary Treatment of Urinary Incontinence (see Summary).

Dargent et al, Gynecol Obstet Fertil 30, 2002, pp. 576-582, Insertion of a sub urethral sling through . . . (see Summary).

Delmas et al, Eur Urol Suppls 2, No. 1, 2003, p. 197, The Transobturator Slingtape Uratape: Anatomical Dangers.

Droupy et al, Eur Urol Suppls 2, No. 1, 2003, p. 197, Trans-Obturator Urethral Support for Female Stress Urinary . . . .

Klingler et al, Eur Urol Suppls 2, No. 1, 2003, p. 197, Severe Complications Following Tensin-Free-Vaginal Tape Procedures.

Delmas et al, Eur Urol Suppls 2, No. 1, 2003, p. 196, #776, The Uratape Transobturator Sling in the Treatment of Female . . . .

de Leval, European Urology, 2003, pp. 1-7, Novel Surgical Technique for the Treatment of Female Stress Urinary Incontinence. . . .

Hermieu et al, Progres En Urologie 13, 2003, pp. 115-117, Plaie vesicale apres bandelette trans-obturatrice.

Delorme, Progres En Urologie 11, 2001, pp. 1306-1313, La Bandelette trans-obturatrice: un procede mini-invasif pour . . . .

de Leval, Urologica Belgica, vol. 52, No. 1, Chapter 147, 1984, Contributions a l'etude du spincter strie de l'uretre chez . . . .

Duckett et al, Journal of Urology, vol. 163, Jun. 2000, pp. 1835-1837, Complications of Silicone Sling Insertion for . . . .

Testut, Traite D'Anatomie Humaine, vol. 5, Ed. 8, 1931, Paris, pp. 460-461.

* cited by examiner

FIG. 3A
FIG. 3B
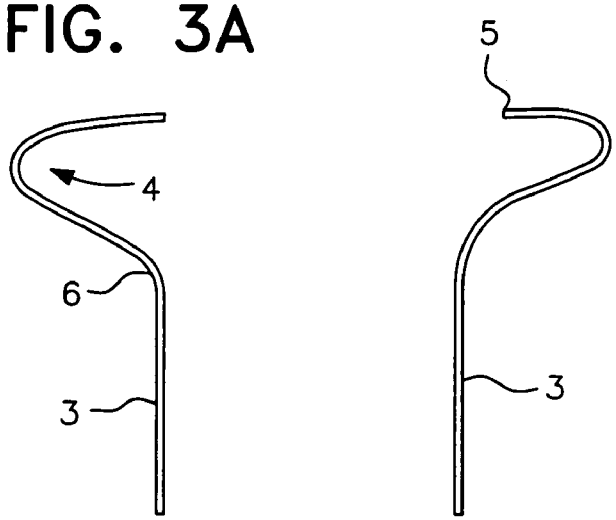
FIG. 3C
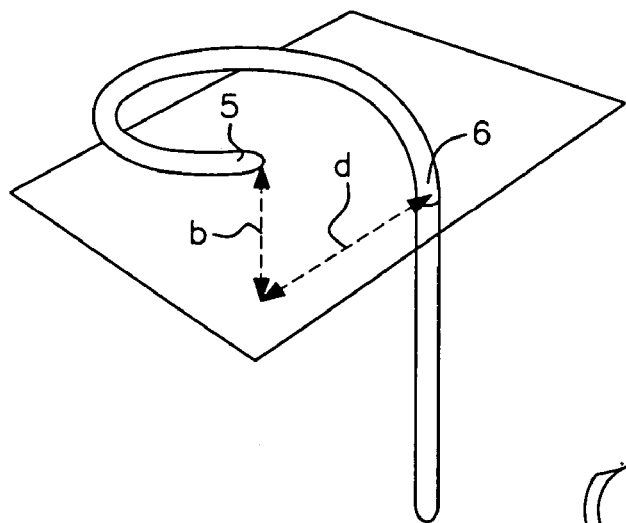
FIG. 3D
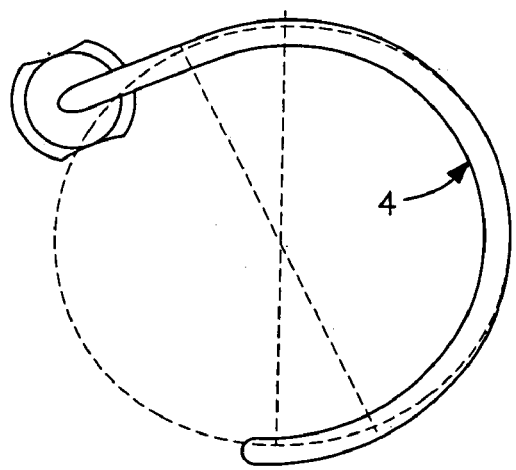

FIG. 4A
FIG. 4B
FIG. 4C
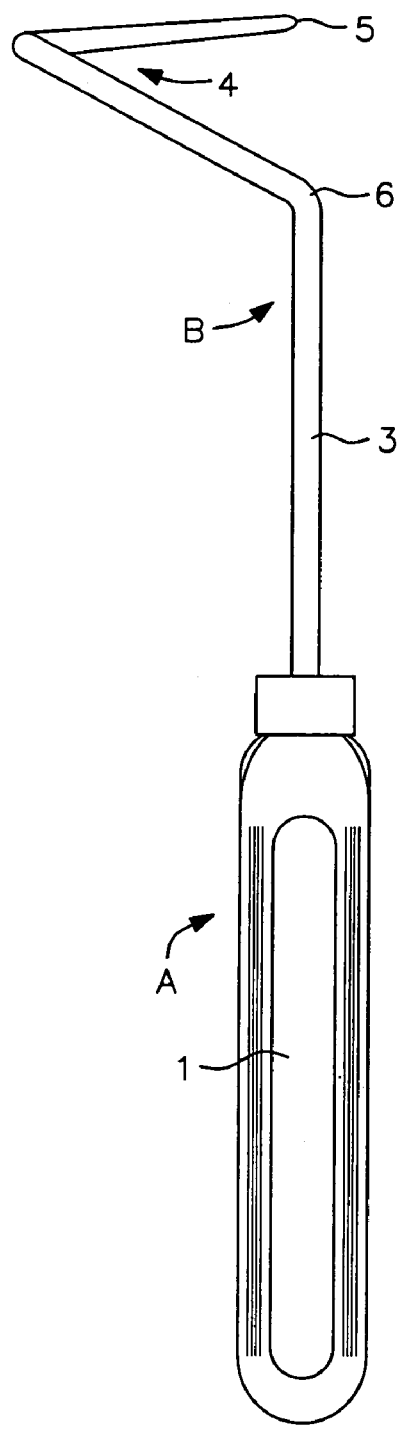
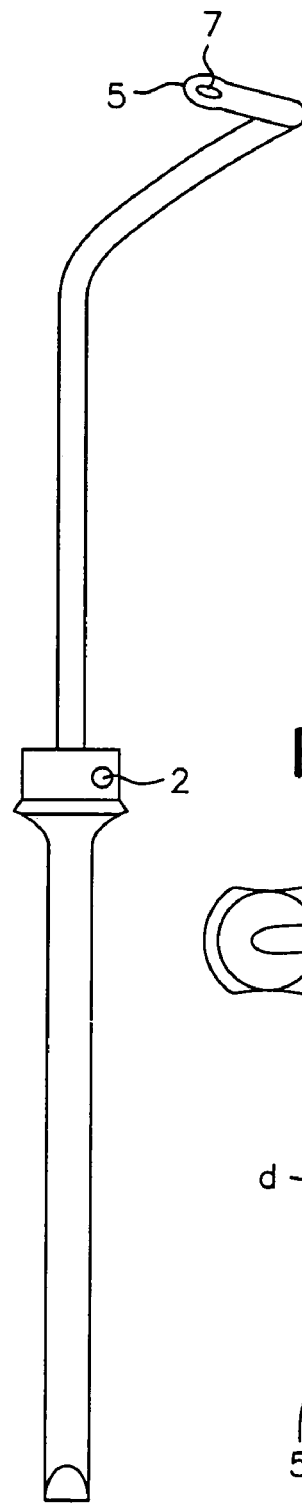
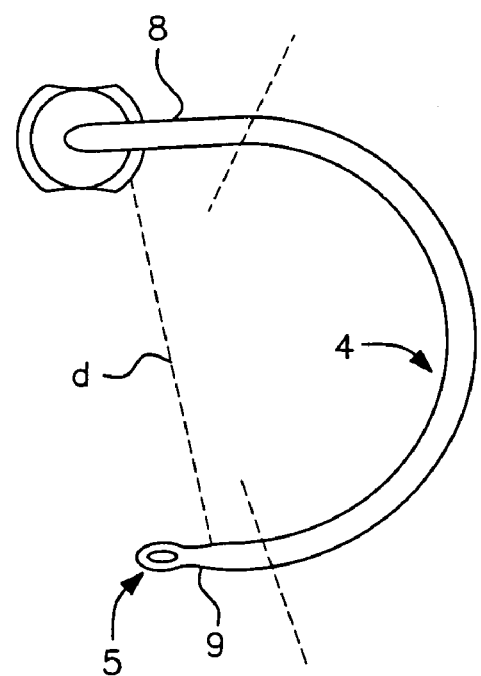

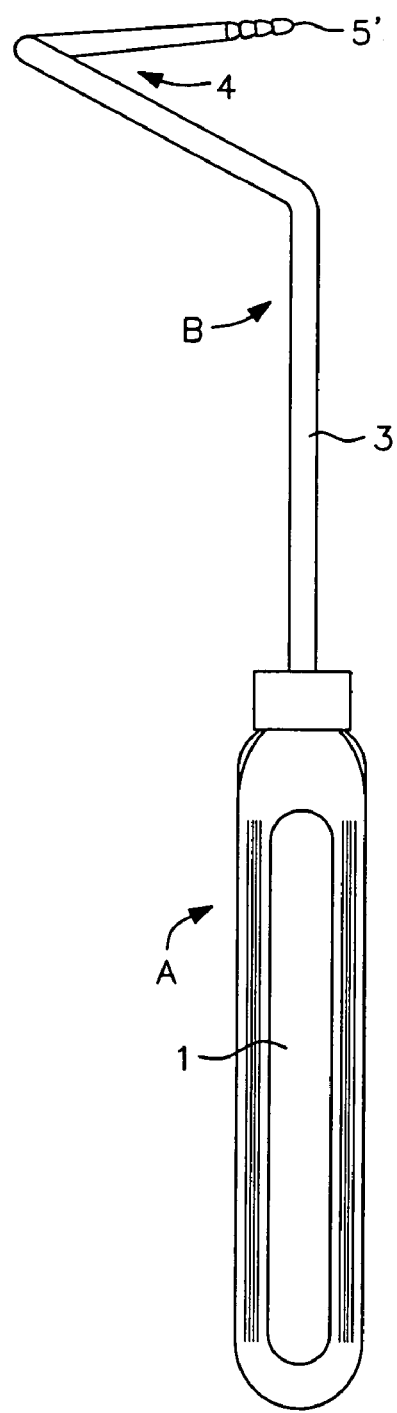
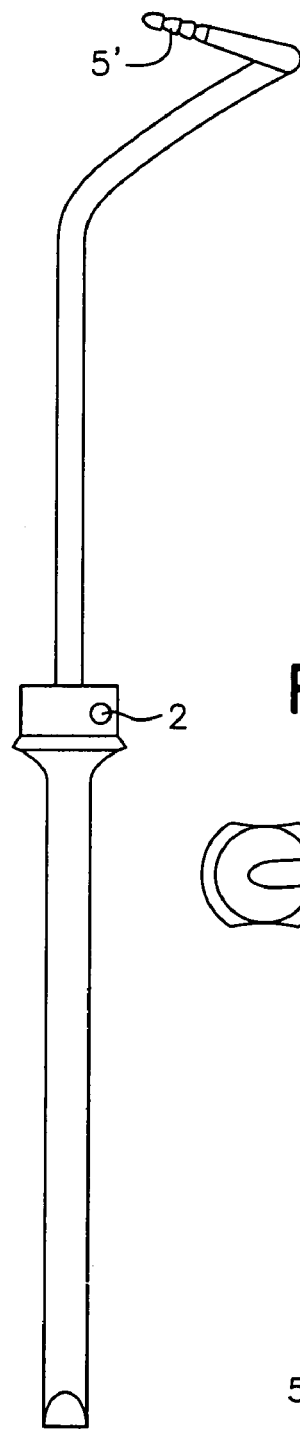
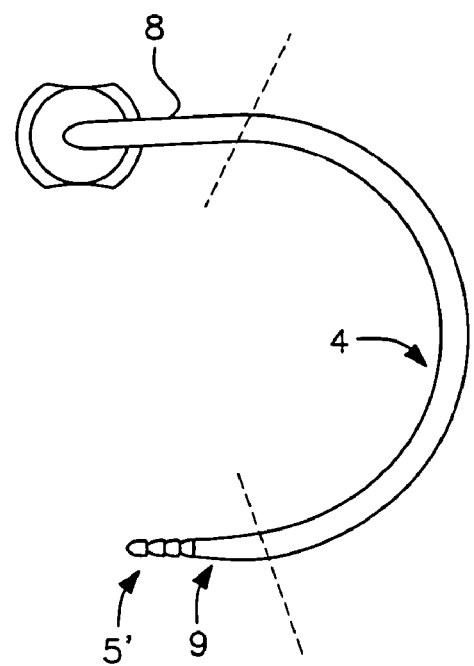

FIG. 6A
FIG. 6B
FIG. 6C
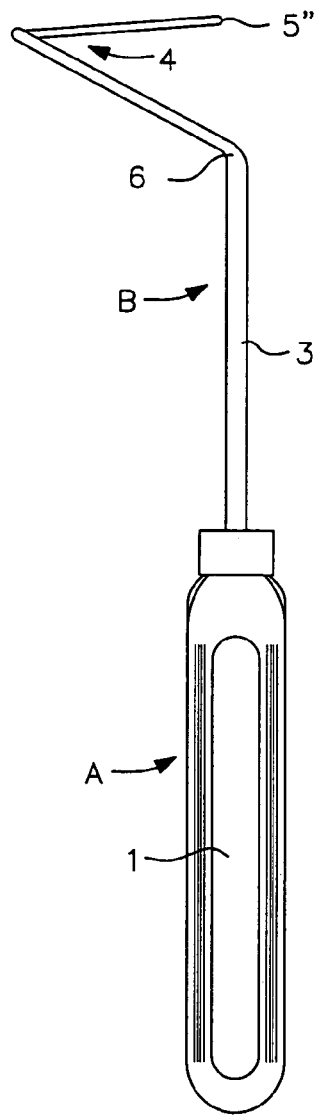
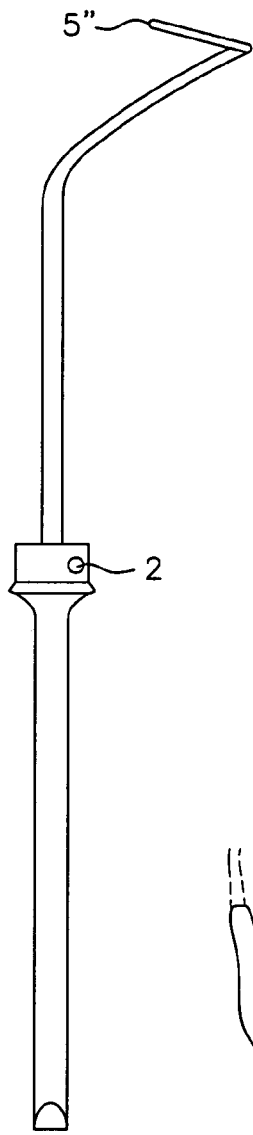
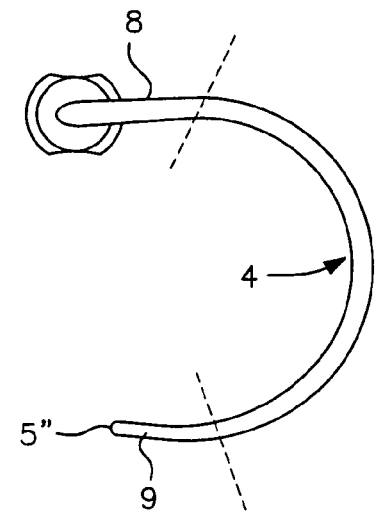
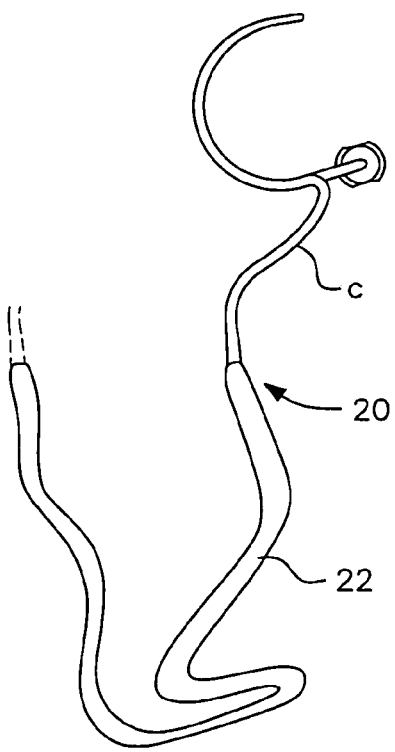
FIG. 6D
FIG. 6E
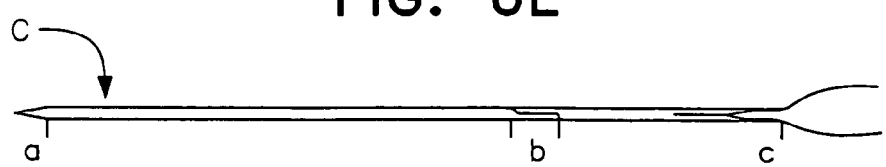

FIG. 7A  FIG. 7B  FIG. 7C  FIG. 7D
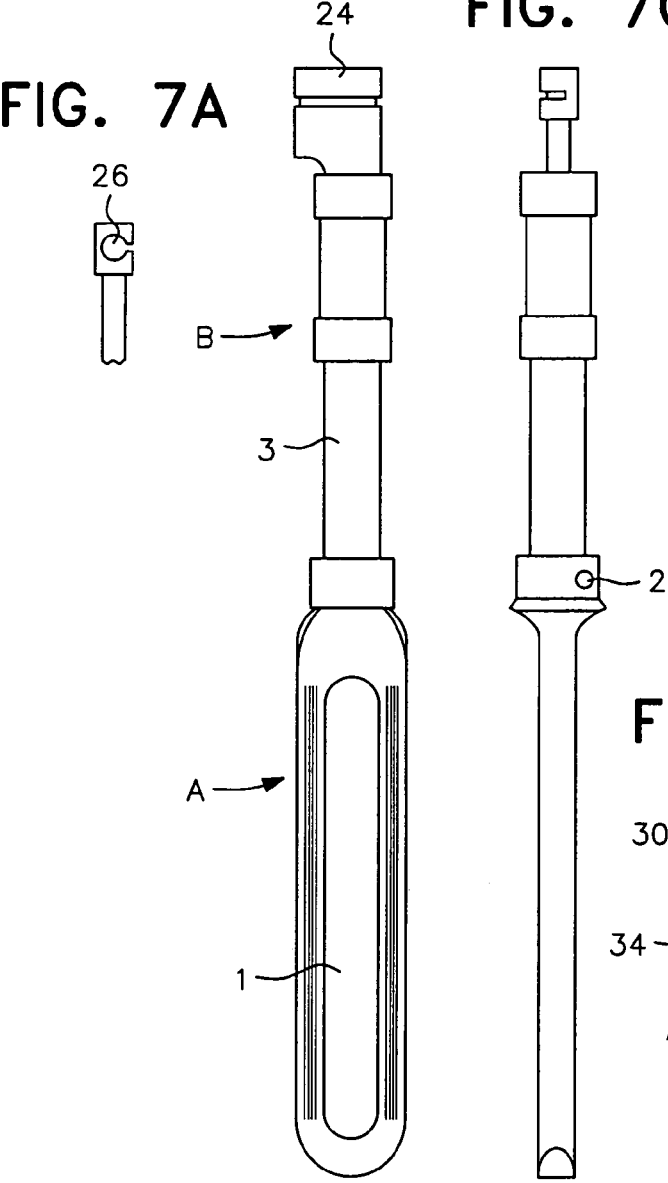
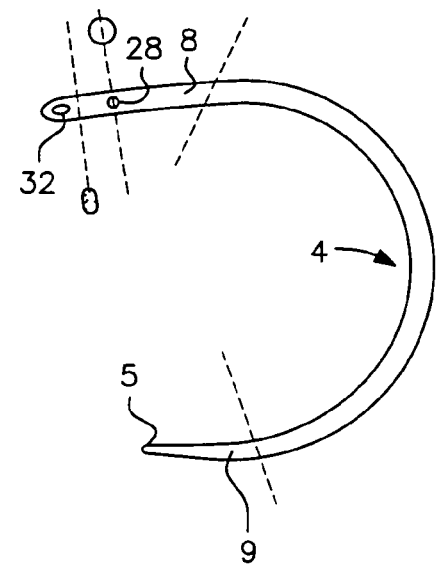
FIG. 7E  FIG. 7F
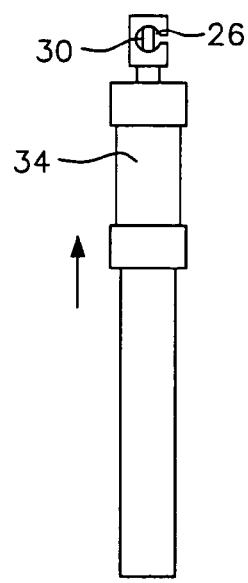
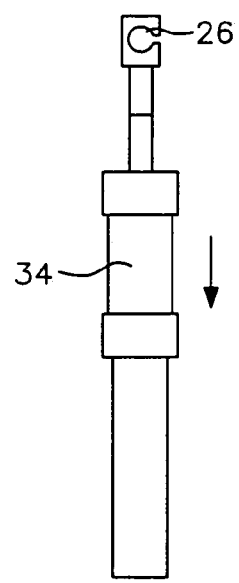

FIG. 9A  FIG. 9B
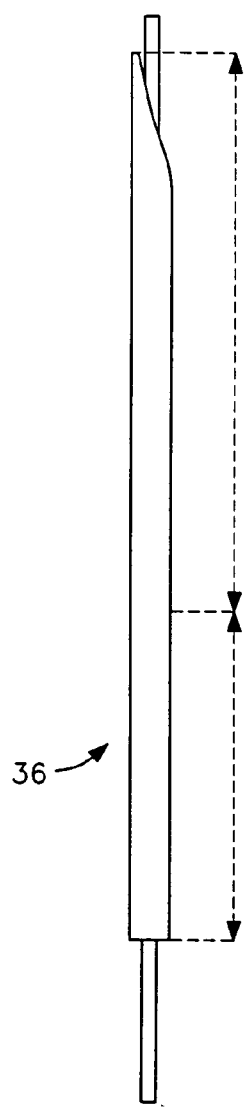
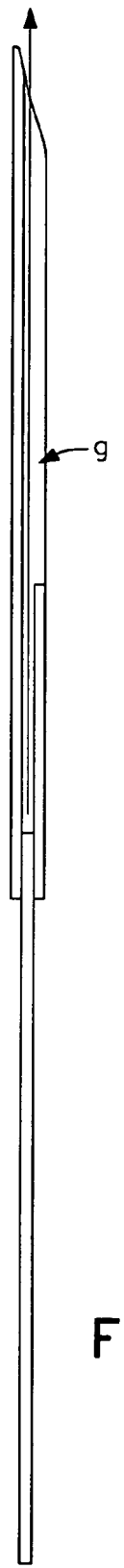
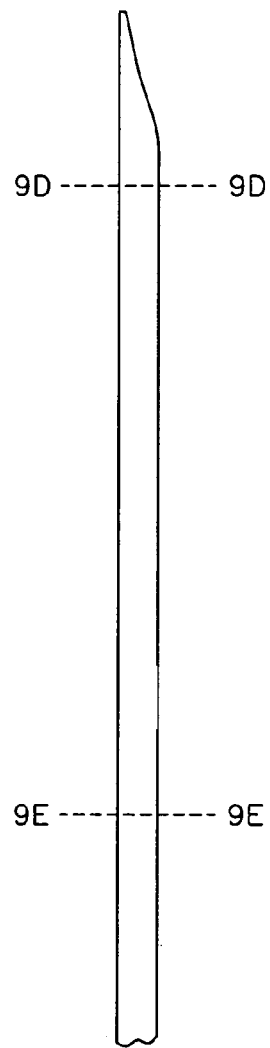
FIG. 9C
FIG. 9D  FIG. 9E
  

SURGICAL PROCEDURE FOR THE TREATMENT OF FEMALE URINARY INCONTINENCE: TENSION-FREE INSIDE-OUT TRANSOBTURATOR URETHRAL SUSPENSION

This application is a continuation-in-part application of U.S. application Ser. No. 10/628,251, filed Jul. 29, 2003, now U.S. Pat. No. 7,204,802 which claims priority from and the benefit of U.S. Provisional Application Ser. Nos. 60/406,674 filed Aug. 29, 2002, 60/419,967 filed Oct. 22, 2002, 60/427,213 filed Nov. 19, 2002 and 60/445,817 filed Feb. 10, 2003, hereby incorporated in their entirety by reference.

FIELD OF THE INVENTION

A new, quick, simple, efficient, safe, and reproducible surgical technique for the treatment of female stress urinary incontinence, in which the posterior urethra is supported using a tape passed through the obturator orifices from inside (underneath the urethra) to outside (thigh folds). A variety of specifically designed surgical instruments are utilized to perform this operative procedure.

BACKGROUND OF THE INVENTION

Understanding of the physiopathological concepts of female stress urinary incontinence (SUI) has consistently improved over the past decades and their application has lead to the development of numerous surgical techniques aimed at curing this disorder. Among these, retro-pubic tension-free vaginal tape (TVT) has probably been the most revolutionary. It has been suggested that retro-pubic TVT may stabilize the mid-urethra at the time of an abdominal pressure increase without modifying cervico-urethral mobility. The use of retro-pubic TVT has been associated with various and relatively frequent per- and post-operative complications, including bladder perforation, temporary or persistent retention, pain, urinary infection, and de novo urgency. Other rare but severe—and possibly underestimated—complications have been reported with this approach. Indeed, the blind passage of the needle in the retro-pubic space can result in injuries to other organs than the bladder, in particular the urethra, vessels, nerves and bowel.

To avoid these complications, alternate approaches with a pre-pubic or transobturator passage of the tape have been developed and continence rates obtained with these routes have been roughly similar to those after the 'classic' retro-pubic TVT. In the transobturator technique described by Delorme et al., Prog. Urol., 11:1306-13, 2001, the tape is inserted through the obturator foramens from outside to inside (in extenso from the thigh folds towards underneath the urethra).

Even though the transobturator outside-in TVT technique is claimed to be a safe procedure, it may occasion urethra and bladder injuries, as reported by Hermieu et al., Prog. Urol, 13:115-117, 2003.

DISTINCTIONS OF THE PRESENT INVENTION OVER THE PRIOR ART

The main differences between the present invention and U.S. Published patent application No. 2002/0099260 relate to:
1. The characteristics of the tape.
2. The operative technique and the surgical instruments employed.
3. The anatomical concepts of the proposed surgery.
4. The physio-pathological aspects of female incontinence.

1. The Tape.

Published patent application No. 2002/0099260 describes a tape made of polypropylene coated in its central region with a substance, such as silicone, which region is intended to be inserted in close vicinity with the urethra and is capable of preventing any adhesion of the surrounding tissues with the tape. The coating of the tape is intended to allow subsequent surgical re-intervention, such as implantation of an artificial sphincter.

One of the objects of the present invention is to restore a fixed bearing-point at the posterior aspect of the urethra, at the border between its middle and inferior thirds. The tape according to the present invention is made, along its entire length, of mono-filament or multi-filament knitted polypropylene. This type of material has been used for several decades for surgical hernia repair, cardiac and vascular surgery, and plastic surgery, for example. This non-absorbable material will be colonized with connective tissue, including fibroblasts, hence allowing the integration of the implant in the tissues. The tape, in the present invention, can be made of synthetic or biological material.

In published patent application No. 2002/0099260, the non-adherent portion of the tape, in its central part, leaves, between the tape and the urethral wall, a space that may favor infection and erosion problems. The literature has described these phenomena of erosion and infection, encountered in 3% of implanted silicone-coated artificial sphincters and, more frequently, when silicone tapes are employed (Duckett, J. R. and Constantine, G.: Complications of silicone sling insertion for stress urinary incontinence., J. Urol. 163(6):1835-1837, 2000).

2. The Operative Technique and the Surgical Instruments Employed.

According to published patent application No. 2002/0099260, after a median vaginal wall incision is made at the level of the middle third of the urethra, the lower internal part of each obturator foramen is identified by a finger slipped into the vaginal incision and an incision is made in the groin skin, so as to form an orifice through which an Emmet needle is then passed from outside to inside (in extenso from the groin folds towards underneath the urethra).

Another of the stated objects of the present invention lies in the fact that the design of the invented surgical tools allows the accurate, safe and reproducible placement of the tape from inside to outside (in extenso from underneath the urethra towards the folds of the thighs). The inventive surgical technique of the present invention does not require any marking of the obturator foramens. The original and specific design of the inventive surgical tools of the present invention, which are spiral-shaped with a lag between the initial and terminal ends of the tools, permits to reliably locate, prior to the passage of the needles, their skin exit points at the groin folds. With the inventive tools of the present invention, the exit points are always located above a horizontal line at the level of the urethral meatus line, and one to three centimeters outside the groin folds.

Contrary to the surgical devices of the present invention, EMMET or DOYEN needles are long needles with variable curve angles, but only in one plane. The same EMMET or DOYEN needle is used for passing the tape through both obturator foramens and the operator needs to guide the needle with his fingers, which renders the passage of the needle less accurate and reproducible.

The inventive tools of the present invention are pairs of instruments, specific for each side. The terminal end of the needles is brought into contact with the upper part of the ischio-pubic branches. At this moment, a simple rotation movement, while keeping the handle of the instrument parallel with the sagittal axis of the vulvar slit, allows the precise exit of the needles. Thus, the operative technique described is much safer. The vaginal wall is carefully dissected under visual control. It is impossible to damage the urethra and the bladder since the needles are directly passed from the perineal to the obturator regions, and then to groin folds, running away from the pelvis. Thus a cystoscopy is not necessary.

The passage of the needles described in published patent application No. 2002/0099260 is different, since the needles cross the levator ani muscles, which belong to the pelvic region. With the technique of the needle's passage described in published patent application No. 2002/0099260, a risk of bladder and urethra perforation subsists.

There have been reports of three patients in whom a sub-urethral tape has been inserted according to the method detailed in published patent application No. 2002/0099260 who developed a subsequent urethral fistula. The treatment of the urethral fistula in two of these patients resulted in complete urinary incontinence. In addition, two patients in whom the insertion of a sub-urethral tape according to the method detailed in published patent application No. 2002/0099260 has resulted in the occurrence of a bladder perforation.

3. The Anatomical Concepts of the Proposed-Surgery.

In published patent application No. 2002/0099260, it is stated that the tape is passed between the Alban fascia and the peri-urethral fascias. For many authors in the scientific literature, the Alban fascia merely represents a dissection plane and does not correspond to any anatomical structure. At the middle third of the posterior aspect of the urethra, the urethral wall is intimately fused with the anterior wall of the vagina. At that location, no specific aponeurosis exists. In particular, the median perineal aponeuris is always lacking as described by L. Testut in G. Doin, editor, Traité d'Anatomie Humaine, Volume 5, ed. 8, Paris, 1931, pp. 460-461.

4. The Physio-Pathological Aspects of Female Incontinence.

By the present invention the function of the tape is to create a median perineal aponeurosis at the posterior aspect of the urethra and to restore at the middle third of the posterior urethra the fixed bearing point that has been previously reported in the literature by de Leval J., in Acta Urol Belg. 52(1):147, 1984. At page 32, it is written that "our works have identified a fixed point, which is a genuine pivot of contraction, from which two segments must be distinguished, one superior, and the other inferior. The anatomical correspondence of this point of confluence is the median perineal aponeurosis".

SUMMARY OF THE INVENTION

A new variety of specific surgical instruments, comprising spirally-shaped, tube-supporting needles, arrow-like tubes, and a introducer, have now been manufactured to perform a new surgical method of treatment of female urinary incontinence, which consists in creating a tension-free inside-out transobturator urethral suspension.

The metallic spirally-shaped, tube-supporting needles are pairs of instruments, specific for the left and right sides. The 'tube-supporting' needles are stainless steel instruments comprising a spirally shaped section and a handle. The spiral section comprises an open circular segment having a 3 cm radius terminated by two linear segments. On a horizontal plane perpendicular to the handle's axis, the gap between the extremities of the spiral section is 2 cm.

The element supported by the "tube-supporting" needle is a high-density polyethylene tube with a sharp pointed distal end. It bears a lateral opening, which allows the insertion of the 'tube-supporting', needle's spiral segment into its lumen. The proximal end of the tube is opened and bound to the tape in its inner portion. A non-absorbable mono-filament polypropylene tape exactly similar to the one used for 'classic' retro-pubic TVT (Gynecare-Ethicon, Somerville, N.J., USA) is used.

The instrument called the 'introducer' is a stainless steel device that comprises two segments: a proximal tubular hollow segment and a distal, semi-circular, 7 cm-long gutter. The introducer acts as a shoe-horn to ease, without danger, the slipping in of the needle, introduced alongside the gutter, from the perineal space through the obturator foramen.

The other surgical instruments needed to carry out the procedure are: a No 3 knife handle with a pointed blade, two Christophe grips, one anatomical forceps with teeth, one pair of fine scissors with a curved end, one pair of Mayo scissors, two 16 cm-long Allis clamps, one 18 cm-long Babcock forceps, one needle-holder, one 16 French Foley catheter, one Vicryl 3/0 suture.

The surgical procedure is generally carried out under spinal anesthesia but may also be performed under general or local anesthesia.

Two grams of third-generation cephalosporin are administered intravenously at the time of anesthesia induction, followed by 1 gram repeated 8 and 16 hours after the procedure.

Accordingly, it is an object of the present invention to perform a surgical method for treating female urinary incontinence, the method including the steps of identifying a surgical exit point on a horizontal line above the urethral plane where a surgical needle will exit at a thigh of a patient, making an incision of the vaginal wall, performing a para-urethral dissection towards the ischio pubic ramus while avoiding a perforation of the vaginal wall, rotating the surgical needle around the ischio pubic ramus, and penetrating the previously identified surgical exit point from inside the patient with a tip of the surgical needle.

In is another object of the present invention to use a surgical needle in treating female urinary incontinence, the surgical needle including a handle, a straight section having two ends, one end of said straight section being connected to said handle, and a spiral section having two ends, one end of said spiral section being connected at a junction to the other end of said straight section, the other end of said spiral section being a free end terminating in a tip.

These and other objects of the invention, as well as many of the intended advantages thereof, will become more readily apparent when reference is made to the following description taken in conjunction with the accompanying drawings.

BRIEF DESCRIPTION OF THE DRAWINGS

FIGS. 3A through 3D schematically illustrate common features of the four different types of surgical needles of the present invention.

FIGS. 4A through 4C schematically illustrate a front, side and plan view, respectively, of a string passing surgical needle of the present invention.

FIGS. 5A through 5C schematically illustrate a front, side and plan view, respectively, of a tube passing surgical needle of the present invention.

FIGS. 6A through 6C schematically illustrate a front, side and plan view, respectively, of a tube supporting surgical needle of the present invention with the tube schematically illustrated in FIG. 6E, and the tube mounted on the surgical needle, with the tube shown connected to a tape, in FIG. 6D.

FIGS. 7A through 7L schematically illustrate a needle holder assembly for releasably supporting a surgical needle with FIG. 7A showing a slot at one end of a vertical section of the assembly, FIGS. 7B and 7C showing, respectively, a front and side view of the needle holder assembly, FIGS. 7D, 7G, 7H and 7I showing a plan view of a needle to be held by the needle holder assembly, FIG. 7E showing a pin extended into the slot of the assembly and 7F showing the pin removed from the slot to facilitate insertion of the surgical needle (shown in FIG. 7D) into the slot, with FIG. 7J showing a truncated needle with cross sectional views of FIGS. 7K and 7L being taken along lines 7-7 and 8-8, respectively.

FIG. 9A schematically illustrates an introducer providing a passage for a surgical needle, FIG. 9B is a longitudinal section of FIG. 9A and FIG. 9C illustrates a portion of the introducer. FIG. 9D is a sectional view taken along line 9D-9D of FIG. 9C. FIG. 9E is a sectional view taken along line 9E-9E of FIG. 9C.

DETAILED DESCRIPTION OF THE PREFERRED EMBODIMENTS

Figure 1:
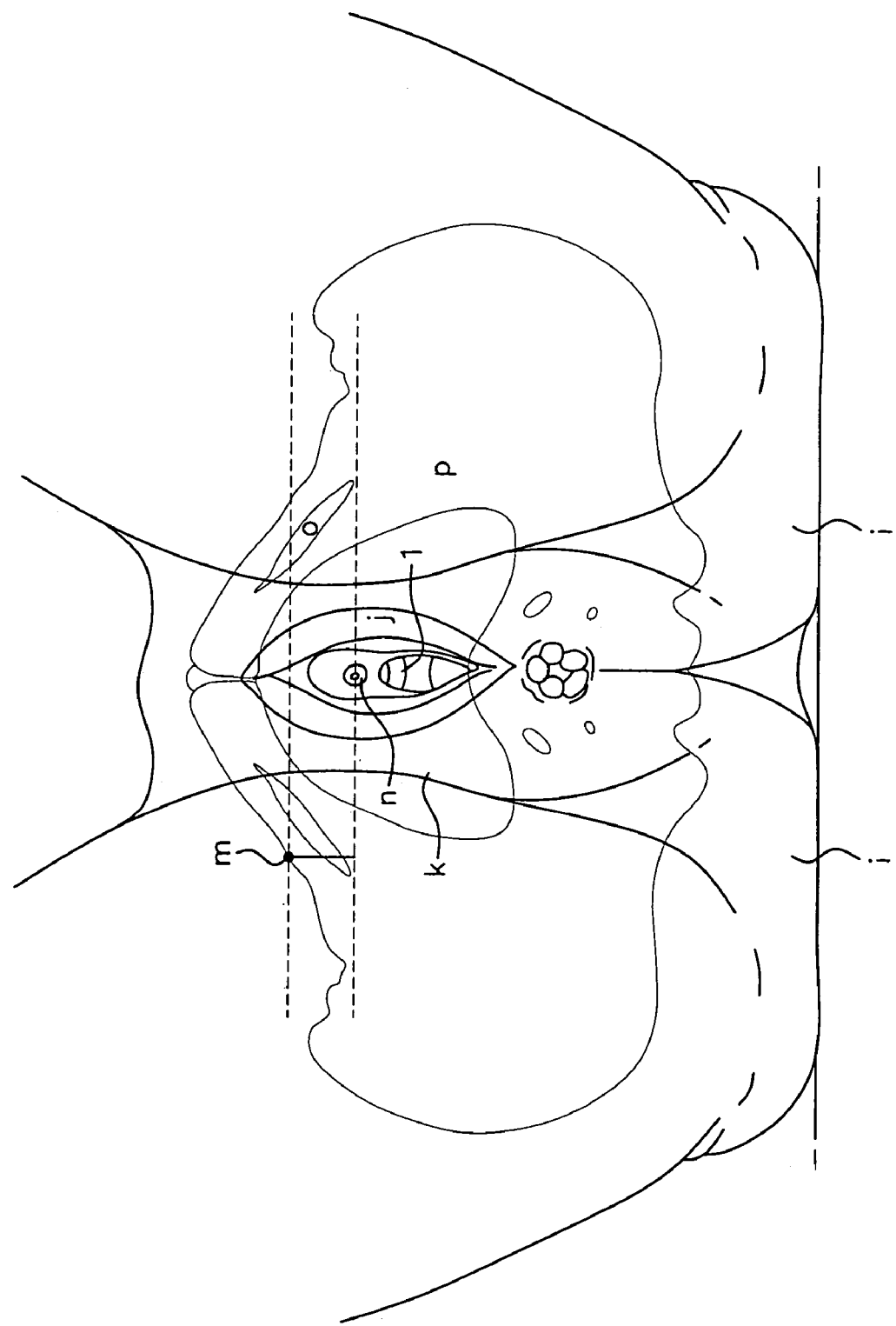
FIG. 1 schematically illustrates the proper positioning of the patient for initiation of the surgical procedure.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

By the surgical procedure of the present invention, the patient is first placed in the gynecological position, legs on stirrups and thighs in hyperflexion. The patient's buttocks (i) reach the edge of the table. The operative field is cleaned with a standard antiseptic agent and draped with multiple drapes rather than a single trousers-shaped drape, with care being taken to keep the groin folds in the operative field. Labia minor (j) are suspended by fixation to the skin with nylon suture a few centimeters above the vulvar ostium, inside the thigh folds, in order to expose the vulva, keeping the groin folds (k) in the operative field. A 16 Fr Foley catheter is inserted into the bladder.

Figure 10A:
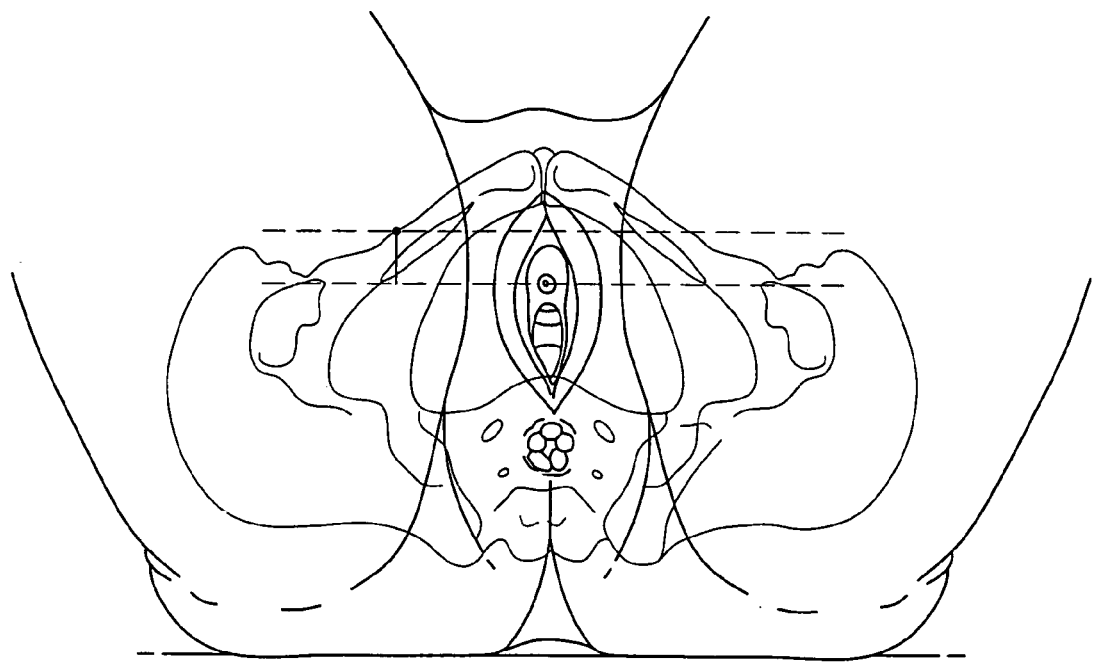
FIGS. 10A, 10B, 11A-11F, 12A and 12B illustrate the preferred procedure using the "tube-supporting" needle along with the arrow-like tubes and the introducer.

The points (m) where the needles will exit at the skin level are identified by tracing a horizontal line at the level of the urethral meatus (n). The exit points are located approximately 1 to 3 centimeters and preferably 2 centimeters above this line, and outside the thigh folds at a distance of 1-4 cm, and preferably 2 cm (see FIGS. 1 and 10A). A 2- to 10-mm skin incision, and preferably 5-mm incision, is made at each exit point.

Figure 10B:
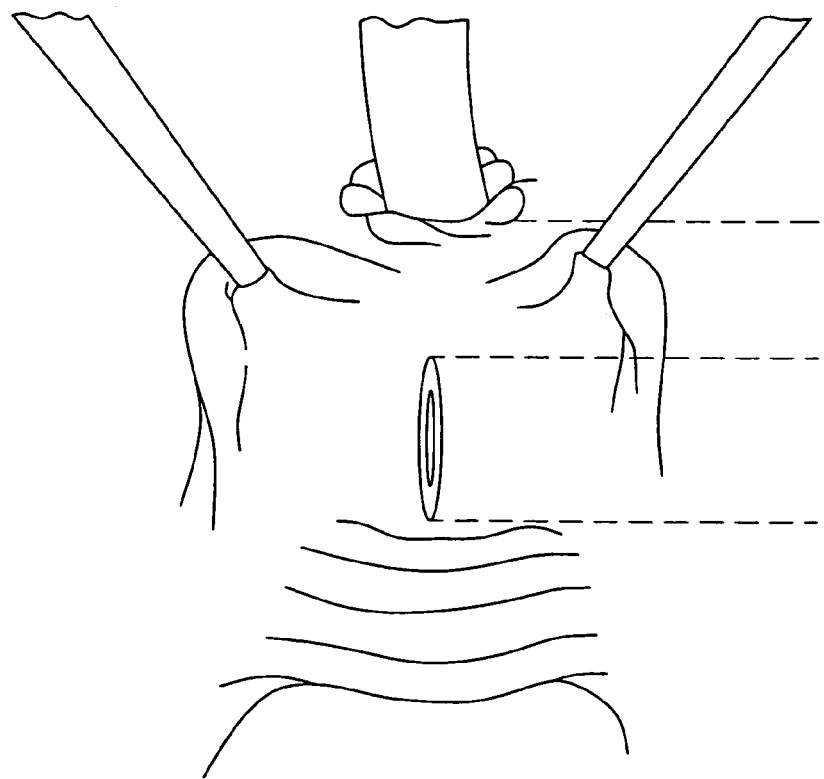
Figure 11A:
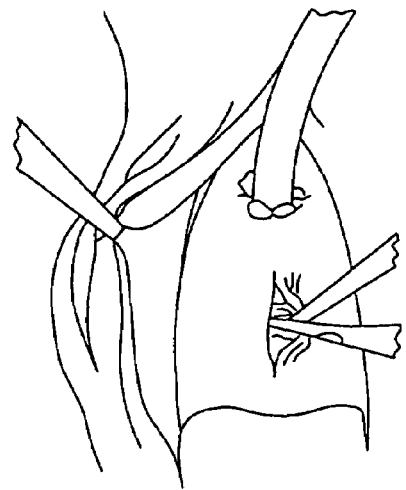

The anterior vaginal wall is suspended with two Allis clamps on either side of the midline, 1 cm proximally to the urethral meatus. A median sagittal incision of the vaginal wall is started at this level and is continued proximally (towards the vaginal pouches) over a 1 cm distance (FIG. 10B). Both vaginal mucosal and sub-mucosal tissues are incised. Minimal para-urethral sub-vaginal dissection is then carried out laterally, with the blade, over a few millimeters distance, on either side (FIG. 11A).

Figure 11B:
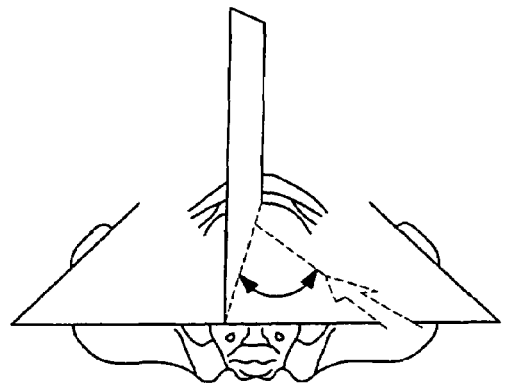
Figure 11C:
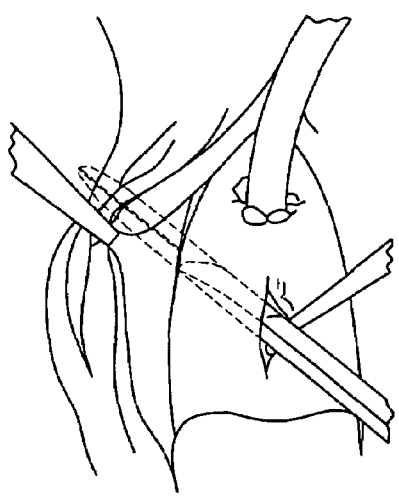

One Allis clamp grasps right minor and major labia while another Allis clamp holds the left margin of the sub-urethral vaginal incision, to clearly expose the most posterior aspect of the right vulvar vestibulum. Fine dissection scissors are introduced through the blade-initiated dissection path, and then further, with a 45° angle relatively to the urethral sagittal plane, towards the upper part of ischio-pubic ramus (FIGS. 11B and 11C). It is important to correctly expose the vulvar vestibulum and to respect the specific direction of the dissection in order to avoid any perforation of the vaginal wall.

Figure 11D:
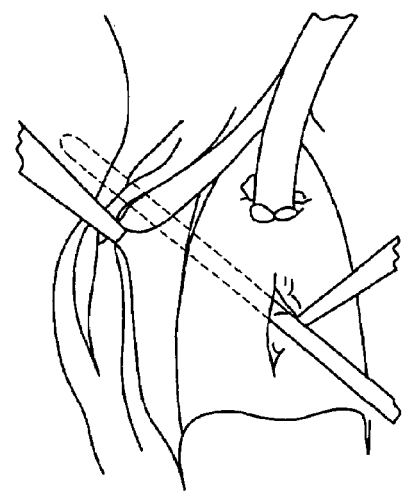
Figure 11E:
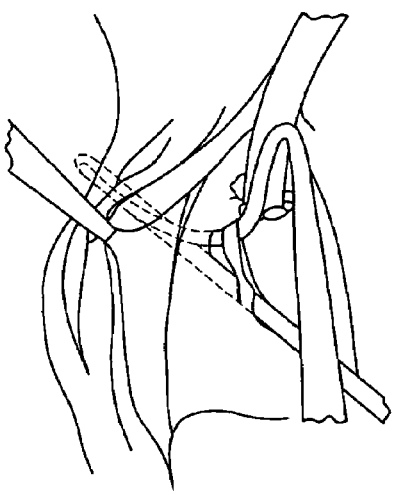
Figure 11F:
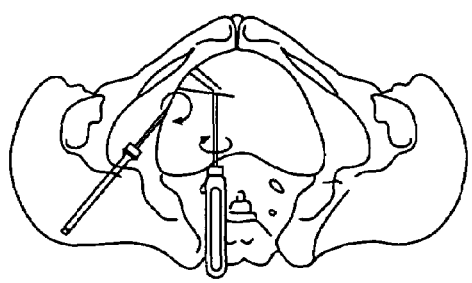

Once the upper part of the ischio-pubic ramus is reached and bone contact is perceived, the right obturator membrane is perforated with the tips of the scissors, which are then slightly opened. During the dissection, bleeding can occur but is never important and only occasionally requires a blood-aspirating device. The introducer is then pushed in the preformed dissection pathway until it reaches and perforates the obturator membrane. The open side of the introducer's gutter must be facing the operator (FIG. 11D). The distal end of the tube is mounted onto the spiral segment of the needle and the assembled device is gently slipped along the gutter of the introducer so as to pass through the obturator foramen (FIG. 11E). The introducer and Allis clamps are removed. At this step, the handle of the needle must be aligned in a parallel manner with the sagittal axis of the vulvar slit. Then, thanks to a rotational movement of the passer, the pointed tip of the tube appears at the previously incised skin exit points at the level of the thigh folds (FIG. 11F). The tube is pulled from the supporting needle, which is removed by a backwards-rotational movement, until the first centimeters of the tape become externalized.

Figure 12A:
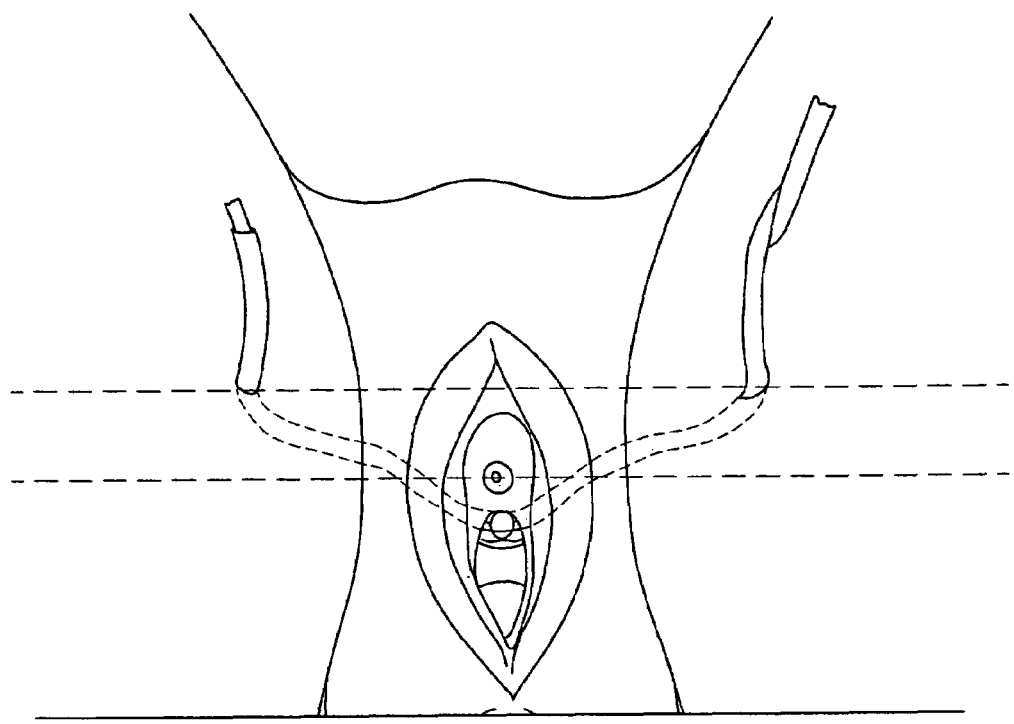
Figure 12B:
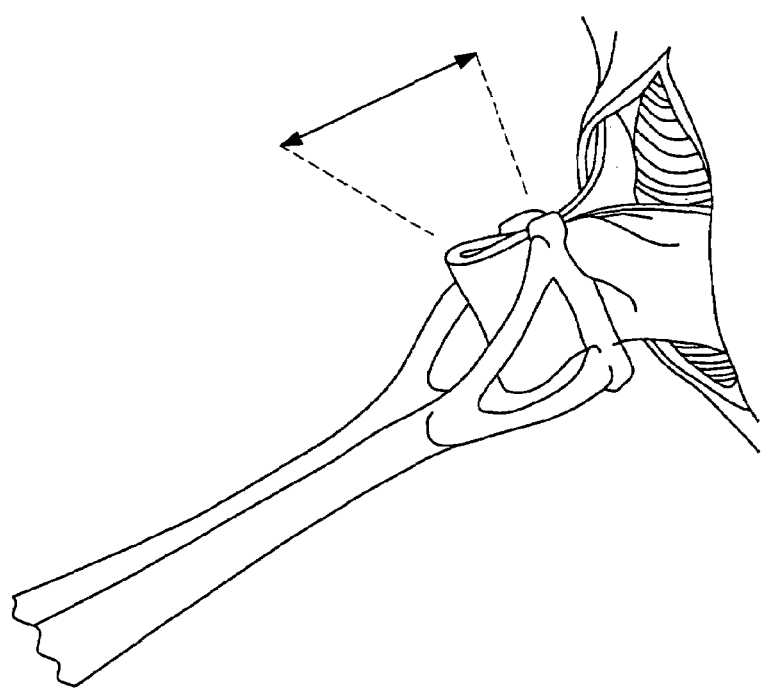

The same technique is applied to the left side, with care being taken not to twist the tape. When both tubes have been extracted through the skin incisions, the ends of the tape are cut. The tape is then aligned under the junction between the mid and distal urethra and the tension of the tape is adjusted by exerting a traction on its two ends and by interposing a pair of scissors between the tape and the urethra so as to leave a space avoiding any tension of the tape. The plastic sheaths are then removed simultaneously (FIG. 12A). An alternative procedure for correctly aligning the tape under the urethra is to grasp the tape at its middle with Babcock forceps so as to create a small, 5 mm-long tape loop (FIG. 12B). As described above, traction is exerted on the distal ends of the tape, which brings the Babcock forceps grasps in contact with the urethra. Plastic sheaths and then Babcock forceps are removed and a small sub-urethral space is thus created between the tape and the ventral aspect of the mid-urethra. The tape ends are cut in the subcutaneous layer and the incisions are closed.

Figure 2A:
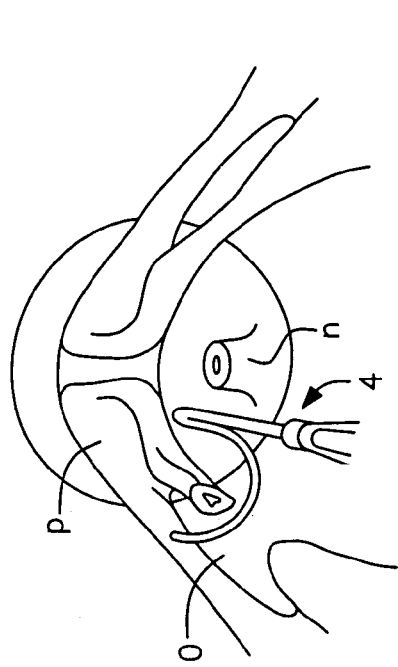
FIGS. 2A through 2D illustrate the trans-obturator passage of the needle and the rotation of the needle around the ischio-pubic ramus from inside to outside.
Figure 2B:
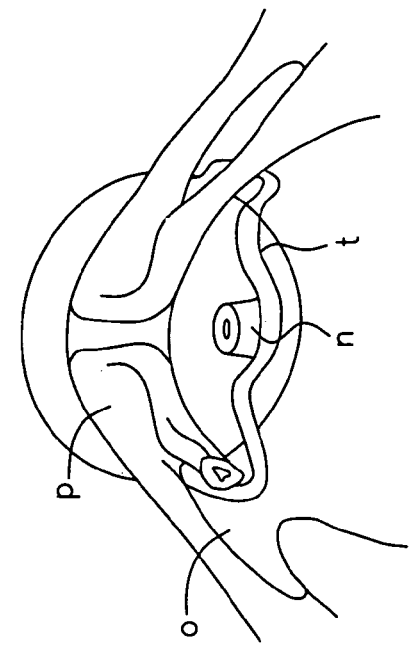
Figure 2C:
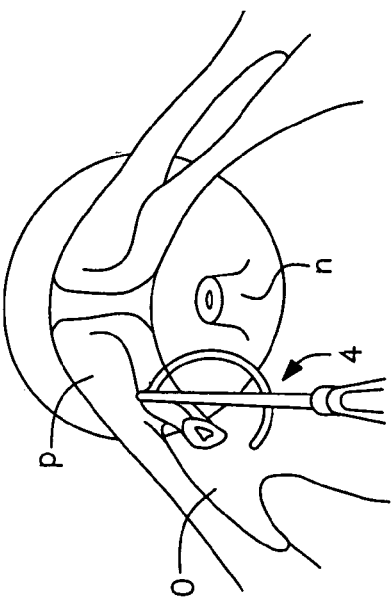
Figure 2D:
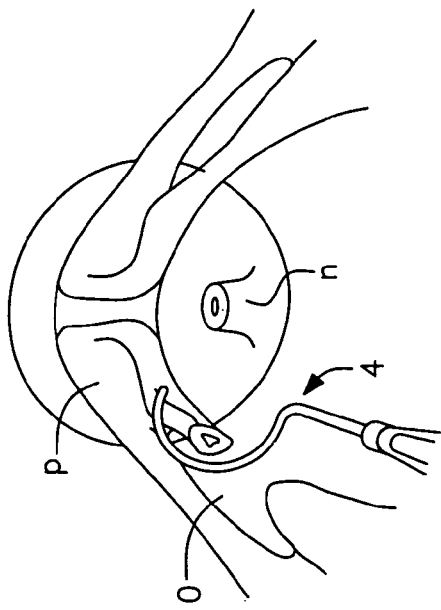

Four different specifically designed surgical needles are used to slide in the sub-urethral tape through the obturator foramens (o). The in-out transobturator passage of the needle 4 is shown in FIGS. 2A-2D. The needle 4 is rotated around the ischio-pubic ramus (p) from inside to outside (in extenso, from a vaginal wound underneath the urethra towards the folds of the thighs) by means of a simple rotational movement (FIGS. 2A, 2B and 2C). The needle perforates the various muscular structures and membrane which fills the obturator hole (o), and, thanks to its spiral design, the tip 5 of the needle appears at the previously defined skin exit point lateral to the thigh fold. The tape (t) is then inserted either directly or indirectly depending on the type of needle used (FIG. 2D).

The four instruments share a common aspect (see FIGS. 3A-3D) which is a spirally shaped needle having a defined design (length, curvature, diameter, shape) supported by a common handle. All these devices have been created to insert the tape from inside to outside (in extenso from a vaginal wound underneath the urethra towards the folds of the thighs), either indirectly ('string-passing' or tube-passing' needles) or directly ('string-passing', 'tube-supporting' and 'needle-holder' needles).

The four surgical needles comprise a flat spiral section 4, with a definite diameter, attached to a vertical section 3 by a junction 6 as shown in FIG. 3A. The flat spiral section 4 comprises an open circular or nearly-circular segment having a length of ½ to ¾ of a circle and an extremity 5 which is located at specific distances "b" and "d" spaced from the junction 6 between the vertical and spiral segments (FIG. 3C). The b and d distances may be varied from up to 3.5 cm for b and from 4 to 8 cm for d. The flat spiral section 4 may also comprise two linear segments 8 and 9 from 1 to 3.5 cm, as illustrated in FIGS. 4 to 7.

In the "string-passing" needle of FIGS. 4A-4C the lower segment A of the device comprises a 5-15 cm, and preferably a 10-cm handle 1 secured to the upper segment of the device with a set screw 2. The upper segment B of the device, which has a 2-5 mm, preferably 4-mm diameter, comprises a 6-18 cm, preferably 12.5 cm flat spiral section 4 attached to a 5-15 cm, preferably 9-cm vertical section 3 at the junction point 6. The flat spiral section is an open, spirally shaped, nearly circular segment, with its end or tip 5 located at a distance d from point 6. The extremity of the spiral segment includes a 3-15 mm, preferably 8-mm long eyelet 7, through which a lace, a string or a tape can be passed. The flat spiral section may comprise two 1-3.5 cm, preferably 2-cm linear segments 8 and 9. The distance d may be varied from 4 to 8 cm.

Alternatively, the upper B and lower A segments of the instrument can be built as one unique segment, without junction parts.

In the 'tube-passing' needle of FIGS. 5A-5C, the lower segment A of the device comprises a 5-15 cm, preferably 10-cm handle 1 secured to the upper segment B of the device with a set screw 2. The upper segment B of the device, which has a 2-5 mm, preferably 4-mm diameter, comprises a 6-18 cm, preferably 12.5-cm flat spiral section 4 attached to a 5-15 cm, preferably 9-cm vertical section 3 at the junction point 6. The flat spiral section is an open, spirally shaped, nearly circular segment, whose extremity or tip 5' has a 5-15 mm, preferably 7-mm long, conic shape and is formed by one to five, preferably three curled segments, enabling the attachment of the tube to the spiral segment. The flat spiral section may comprise two 1-3.5 cm, preferably 2-cm linear segments 8 and 9.

Alternatively, the upper B and lower A segments of the instrument can be built as one unique segment, without junction parts.

In the 'tube-supporting' needle of FIGS. 6A-6D, the 'tube-supporting' device enables the direct passage of the tape from inside to outside in one unique rotational movement. The instrument supports a novel element, which is an arrow-like tube whose distal end is closed and pointed. The tape is bound in the inner portion of the proximal end of the tube.

The lower segment A of the device comprises a 5-15 cm, preferably 10-cm handle 1 secured to the upper segment B of the device with a set screw 2. The upper segment B of the device, which has a 2-5 mm, preferably 3 mm diameter, comprises a 4.5-17.6 cm, preferably 11.8-cm flat spiral section 4 attached to a 5-15 cm, preferably 9-cm vertical section 3. The flat spiral segment of the 'tube-supporting' needle is in general 0.4-1.5 cm, preferably 0.7 cm shorter than the spiral section of the 'string-passing' or 'tube-passing' needles. The flat spiral section is an open, spirally shaped, nearly circular segment, whose distal extremity or tip 5" is flat. The flat spiral section may comprise two 1-3.5 cm, preferably 2-cm linear segments 8 and 9.

Alternatively, the upper B and lower A segments of the instrument can be built as one unique segment, without junction parts.

Figure 8A:
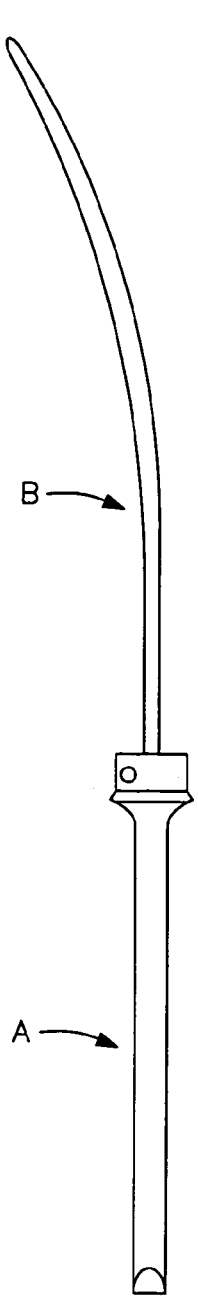
FIGS. 8A, 8B and 8C schematically illustrate a side, front and top plan view, respectively, of an alternate embodiment of a straight tube supporting surgical needle with the arrow-like tube being shown in FIG. 8E and mounted on the needle, having the tube connected to the tape, in FIG. 8D. The straight tube-supporting needle is intended to pass the tape in the retro-pubic space.
Figure 8B:
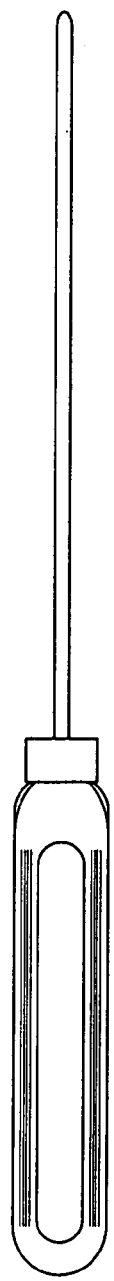
Figure 8C:
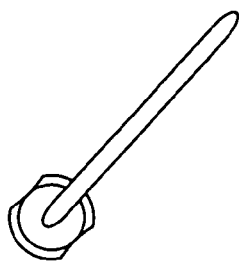
Figure 8D:
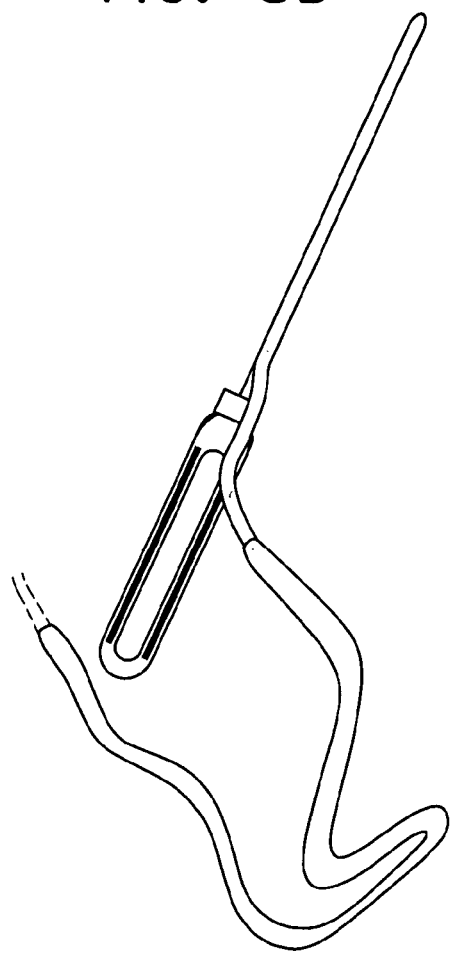
Figure 8E:
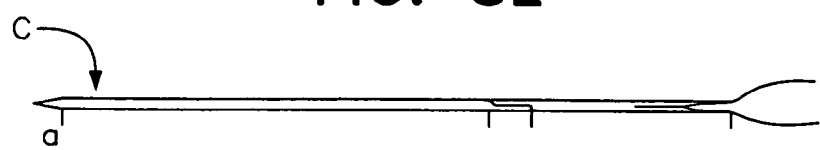

The element supported by the 'tube-supporting' needle as shown in FIGS. 6E and 8E is an arrow-like tube C, which is commonly but not exclusively made of high density polyethylene and has a length of 10-25 cm, preferably 17 cm. The inner diameter of the tube is 2.0-4.5 mm, preferably 3.3 mm and its outer diameter is 3.0-5.5 mm, preferably 4.3 mm. The wall of the tube is 0.3-0.8 mm, preferably 0.5 mm thick. The distal end of the tube has a length of 3-40 mm, preferably 7 mm, is sharp with the pointed part having a 3-20 mm, preferably 5 mm length. The tube bears a lateral opening which is 5-20 mm, preferably 10 mm long and is located at 10-20 cm, preferably 12.5 cm from the distal end of the tube. This lateral opening enables the introduction of the spiral segment 4 of the needle into the tube as shown in FIG. 6D. The proximal end 20 of the tube C is bound in its inner portion to the tape 22.

It is possible that removal of the segment of the tape that passes through the adductor muscles would cause less post-operative pain. To avoid this possibility, the tape length would be reduced to approximately 12 centimeters. Both ends of the tapes would be attached to a nylon suture, creating a loop at the tape's ends, and ending as a single string at its distal extremity.

Figure 6F:
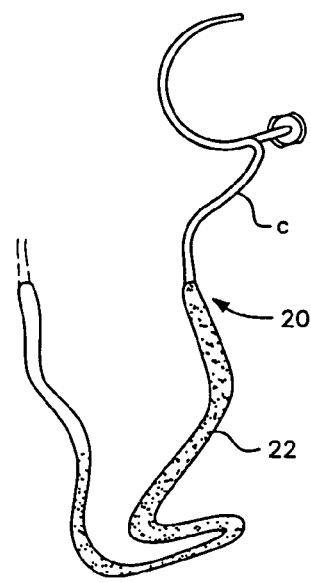
FIGS. 6F through 6I schematically illustrate alternate embodiments of a tube supporting surgical needle using a surgical tube and tape.
Figure 6H:
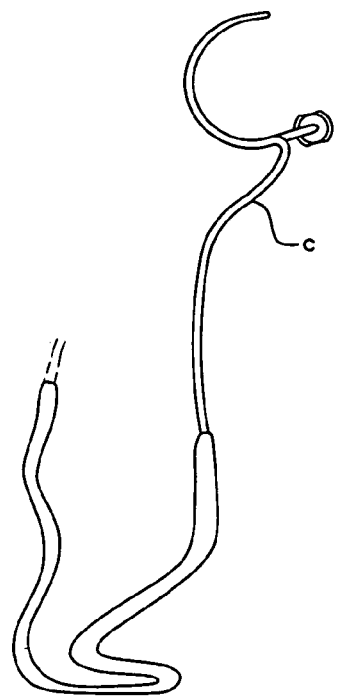
Figure 6G:
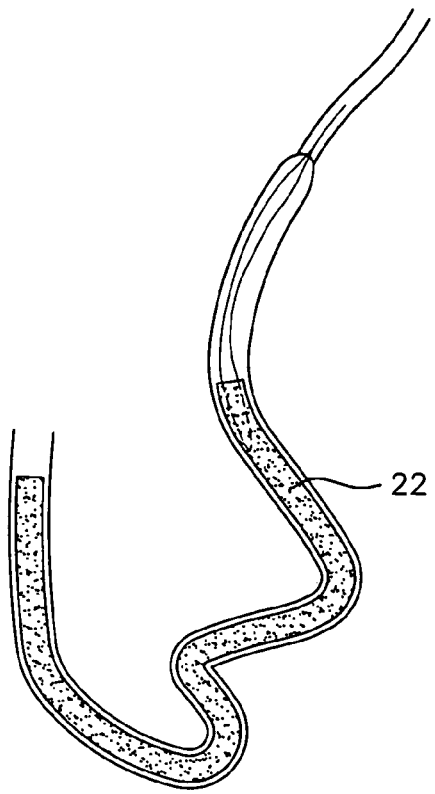
Figure 6I:
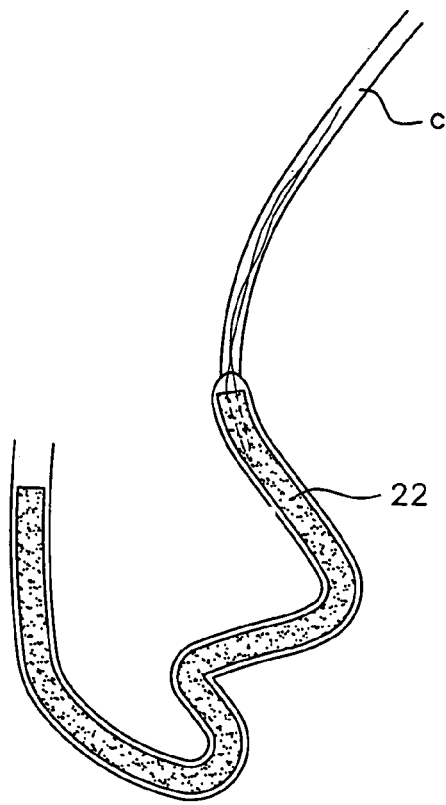

To improve the device shown in FIG. 6D, two possibilities exist:

a) either include the nylon suture in the sheath over an approximate 18 cm distance (FIGS. 6F and 6G), b) or make the tube approximately 18 cms longer (FIGS. 6H and 6I).

The surgical procedure using the device of FIG. 6F-6I would remain the same as the one described for FIG. 6D, and the tape would traverse only the obturator muscles and membrane. In this way, urethral support would be sufficient.

In the 'needle-holder' device, as shown in FIGS. 7A-7F, the 'needle-holder' device comprises a unique segment with a handle 1 and a pair of needles at the ends of which the tape is attached. This device enables to slip in the tape from underneath the urethra towards the obturator foramens (in extenso, from inside to outside) in one single rotational movement.

The lower segment A of the device comprises a 5-15 cm, preferably 10-cm handle 1 secured to the upper segment 3 of the device with a set screw 2. The upper segment B of the device is divided into two elements: the vertical section 3 and the spiral section 4. The vertical section comprises, at its distal end 24, a slot 26 in which the proximal end of the spiral section 4 of the needle shown in FIG. 7D can be inserted and then secured in place by a pin system. The spiral section 4, an open spirally shaped, nearly circular segment, is 6.0-18.0 cm, preferably 12.5-cm long and has a 2-5 mm, preferably 4-mm diameter. Its distal extremity or tip 5 is pointed. The flat spiral section may comprise two 1-3.5 cm, preferably 2-cm distal linear segments 8 and 9. The proximal segment 8 of the spiral section, which may also be linear, includes a small slot 28 enabling the insertion of pin 30, as well as an eyelet 32 designed for the attachment of the tape to the spiral section.

Pin 30 is inserted in slot 28 by movement of a section 34 of vertical section 3 as shown in FIGS. 7E and 7F. The at rest position of FIG. 7E shows pin 30 ready to engage in slot 28 when spiral section 4 is inserted into slot 26 after retraction and then extension of section 34 as shown in FIG. 7F.

The spiral section of the 'needle-holder' needle, to which the tape is attached, can be displaced from its supporting handle once it has been passed through the obturator orifice and the skin by means of one single rotational movement from inside (underneath the urethra) to outside (the groin folds).

Figure 7G:
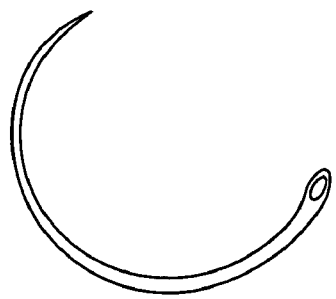
Figure 7H:
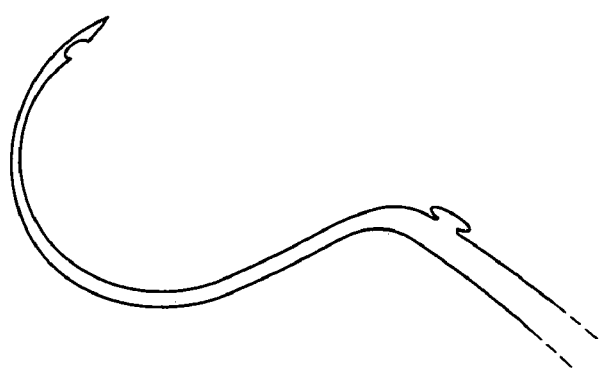

To perform the tension-free inside-out transobturator urethral suspension one may also use a needle-holder as shown in FIG. 7A with the needle having an eyelet at its proximal end as shown in FIG. 7G having the same shape and diameter as those of the string-passing needle in FIG. 7D, but with a thickness of only approximately 2 mms. The needle would be simply slipped in the gutter of the guide and turned around the ischio-pubic ramus as one rotates the needle-holder. One alternate would be to pass a Reverdin's needle as shown in FIG. 7H in the introducer's gutter. In both cases, the insertion can be carried out directly (suture inserted in the eyelet before rotation of the needle).

Figure 7I:
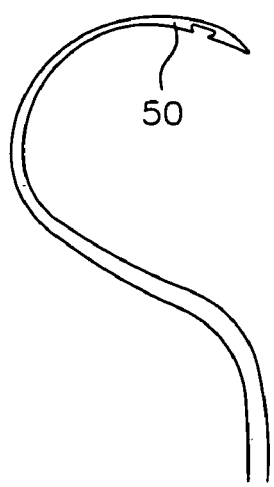

Modifications of the string-passing needle and of the tape: the last five centimeters 50 of the string-passing needle as shown in FIG. 7I would have a thickness reduced to approximately 2 mms. A suture would be introduced in the eyelet and an approximate 12 cm tape prolonged with the nylon suture would be pulled in the perineal track (from inside to outside, with direct insertion). The sheath would need to be removed at the vaginal level.

Figure 7J:
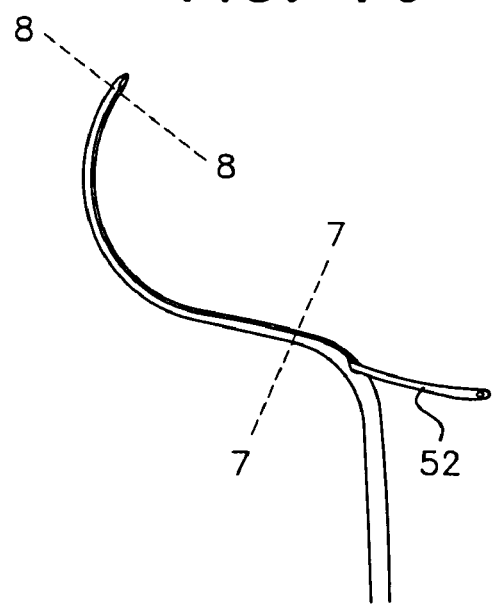
Figure 7K:
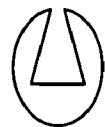
Figure 7L:

In another example, as shown in FIG. 7J, the distal end of the spiral needle would be 5 cms shorter, and this spiral needle would include a small gutter as shown in cross section taken along line 7-7 in FIG. 7K and along line 8-8 in FIG. 7L, bearing a distal orifice, to allow the passage of a thin needle 52. At its distal extremity, the gutter inside the spiral needle would present an angulation, so that the thin needle passed in the gutter would exit more medially in the thigh.

Once the pre-passage has been formed by the scissors in the obturator membrane, from underneath the urethra towards the ischio-pubic ramus, one may encounter some difficulty to slip in the needle of these newly designed devices through this pre-passage. An instrument, called the 'introducer', as shown in FIGS. 9A-9C, may ease the passage of the needles in the perineal region, towards the obturator membranes. This instrument, which is 9-15 cm, and preferably 11 cm long, comprises two segments: a proximal 2-7 cm, and preferably 4 cm long, 3-6 mm, and preferably 4 mm diameter, tubular segment 34 and a distal, semi-circular, 5-11 cm, and preferably 7-cm long, 3-6 mm, and preferably 4-mm diameter, gutter g. The gutter of the introducer is brought into contact with the upper part of the ischio-pubic ramus. The needles are introduced alongside the gutter, which plays the role of a shoe-horn to ease the slipping in of the needle towards the obturator foramen.

When the 'string-passing' (FIG. 4) or the 'tube-passing' (FIG. 5) needles are used for the procedure, a pre-passage in the obturator membrane has to be made with the scissors prior to the passage of the needles. Then, the needle is rotated around the ischio-pubic ramus (p). The needle perforates the various muscular structures and membrane which fill the obturator hole (o), and, thanks to its spiral design, the tip of the needle appears at the previously defined skin exit point lateral to the thigh fold. The same procedure is repeated at the controlateral side with an oppositely curved needle.

On both sides, a string or a tube is attached to the tip of each 'string-passing' or 'tube-passing' needle, respectively. The needle, together with the string or the tube, is rotated back towards the sub-urethral vaginal opening. A synthetic (or biological) tape, which is commonly but not exclusively made of polypropylene, is then tightened to the string or to the tube at its urethral side. The tape is then slipped in from inside to outside, on both sides, by pulling the string or the tube from its skin end.

The same technique can be applied when the 'tube-supporting' (FIG. 6) or the 'needle-holder' (FIG. 7) needles are used. In these two needle variants, the tape, which is attached directly to the tube or to the needle, can be passed directly from below the urethra to the exit points by applying a simple rotational movement on the handle which supports the needle on both sides. Additionally, the end of the needle can be detached from the handle once passed through the obturator foramen (see FIG. 7).

Whichever needle design used, once the procedure has been completed, the tape is correctly positioned underneath the mid-urethra with care being taken not to twist or deform the tape as a cord. No tension has to be exercised on the ends of the sling so that a space remains between the tape and the posterior aspect of the urethra. The introduction of a pair of scissors in the interstice can readily control this space between the urethra and the tape.

Whenever the tape is wrapped in plastic sheaths, these wrappings have to be removed once the tape has been passed through on each side. The tape is cut at the level of the skin exit points without any further fixation. The vaginal and skin incisional wounds are closed with sutures.

The 'straight tube-supporting' needle shown in FIGS. 8A-8F is a modification of the 'tube-supporting' needle described above and permits to slip in the arrow-like tube described in FIGS. 6E and 8E, which is attached to the tape. This device has been designed to insert the tape from downside (in extenso, underneath the urethra) to upside (in extenso, pre- or retro-pubic region). The device comprises a handle A attached to a sagitally curved, 12-18 cm, preferably 15 cm long, 2.5-3.5 mm, preferably 3 mm thick upper segment B, which supports the tube attached to the tape C. The "straight tube-supporting" needle, like all other needles herein described, can be built as one unique, disposable segment.

EXAMPLES

A total of 107 patients were consecutively operated on using the above-detailed surgical procedure. Surgery was carried out under spinal, general, and local anesthesia in 82, 24, and 1 cases, respectively.

Mean age of the patients was 62±12.6 years (median=62 years; range=29-88) and mean parity was 2.54±1.7 (median=2.5; range=0-9). Seventeen patients (15.9%) had been operated previously for incontinence and/or vaginal prolapse.

Most patients (n=74; 69.2%) suffered from typical symptoms of SUI, documented by detailed history, physical examination, endoscopic assessment and urodynamic testing. Ulmsten's test was positive in every case. The other patients (n=33; 30.8%) had associated pelvic organ prolapse. In this group, 45.4% of the patients had genuine SUI and 54.6% had potential SUI.

All patients had a follow-up visit at one month after surgery, with detailed interview, clinical examination, urine analysis, and postvoid residual determination.

The procedure was carried out in all 107 consecutive case subjects, independently of the patient's size and weight. Each of the 214 needles was passed through the obturator foramens and exited at the skin level exactly where it had been marked and incised.

Mean operative time was 14 min (median=13; range=7-20) in case of isolated SUI treatment. Patients with TVT operations only were hospitalized for a mean of 1.8 days (range 0.5-8 days).

No major peri- or post-operative complication was encountered. No injury to the urethra, bladder, nerves or bowel was noted. Significant (>100 mL) intra-operative bleeding did not occur. In none of the cases was the vaginal wall perforated during the operation. No ecchymose or hematoma was noticed after the procedure.

Only few and minor complications were observed. Postoperative minor vaginal erosion was noted in one patient. Three patients (2.8%) had complete retention; two of them had undergone associated prolapse surgical treatment. In these patients, a tape release procedure was carried out in the immediate postoperative period with local anesthetic injection and intravenous sedation as needed. No tape required to be sectioned. None of the patients who underwent a tape release procedure developed incontinence or fistula.

Seventeen patients (15.9%) complained directly after the procedure that they had moderate pain or discomfort in the thigh folds. This symptom usually abated within 2 days and was in all cases controlled by nonopioid antalgics. In 2 patients (1.9%), more severe pain persisted for one week and was associated with hip arthralgia, probably as a result of the gynecological position during the procedure.

Superficial vein thrombosis occurred in one patient developed at day 8 after surgery, with secondary development of an abscess that required drainage. Evolution of this patient was favorable. Since the occurrence of this adverse event, care was taken to prophylactically administer powerful antibiotics in all patients undergoing the surgical treatment.

This analysis mainly focuses on the reproducibility and early complication rates associated with the newly developed surgical procedure and tools of the present invention. At one month after the procedure, the postoperative evaluation showed that 95 of the 107 patients (88.8%) were cured of SUI. Another 8 patients (7.5%) were improved and there were 4 failures (3.7%). Patients not cured by the procedure were incontinent directly after the procedure. A few patients (n=9; 8.4%) exhibited de novo urgency at 1 month after the intervention. At the opposite, some patients (n=33; 30.8%) who had urgency before the operation noted a reduction in the importance of this symptom after the procedure.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A surgical method for treating female urinary incontinence, said method comprising:
    identifying a surgical exit point on a horizontal line above the urethral plane where a surgical needle will exit at a thigh of a patient,
    making an incision of the vaginal wall,
    performing a para-urethral dissection towards the ischio pubic ramus while avoiding a perforation of the vaginal wall,
    inserting a leading tip of a spiral section of the surgical needle into a lateral opening of a hollow tube to cover the leading tip of the spiral section of the surgical needle while the surgical needle is completely outside the patient, the lateral opening of the hollow tube being located spaced between a sharp pointed distal end and a proximal end of the hollow tube, the lateral opening being located 10 to 20 cm from the sharp pointed distal end of the hollow tube, and a tape being bound to the hollow tube at the proximal end of the hollow tube,
    inserting the spiral section of the needle with the tube over the leading tip of the spiral section into the patient,
    rotating the spiral section of the surgical needle around the ischio pubic ramus, and
    penetrating the previously identified surgical exit point from inside the patient with the leading tip of the surgical needle and the tube moving from first inside the patient to then outside the patient by a single rotation of the surgical needle.

2. The surgical method as claimed in claim 1, wherein a length of the tape is approximately 12 cm.

* * * * *

UNITED STATES PATENT AND TRADEMARK OFFICE
CERTIFICATE OF CORRECTION

PATENT NO. : 7,611,454 B2 Page 1 of 1
APPLICATION NO. : 10/854140
DATED : November 3, 2009
INVENTOR(S) : Jean De Leval It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1132 days.

Signed and Sealed this

Twelfth Day of October, 2010

David J. Kappos
*Director of the United States Patent and Trademark Office*